US011484765B2

(12) United States Patent
Takenaka

(10) Patent No.: US 11,484,765 B2
(45) Date of Patent: Nov. 1, 2022

(54) WALKING SUPPORT SYSTEM, WALKING SUPPORT METHOD, AND PROGRAM

(71) Applicant: HONDA MOTOR CO., LTD., Tokyo (JP)

(72) Inventor: Toru Takenaka, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 526 days.

(21) Appl. No.: 16/492,318

(22) PCT Filed: Mar. 22, 2018

(86) PCT No.: PCT/JP2018/011375
§ 371 (c)(1),
(2) Date: Sep. 9, 2019

(87) PCT Pub. No.: WO2018/174151
PCT Pub. Date: Sep. 27, 2018

(65) Prior Publication Data
US 2020/0276490 A1 Sep. 3, 2020

(30) Foreign Application Priority Data

Mar. 22, 2017 (JP) .............................. JP2017-055720

(51) Int. Cl.
A63B 71/06 (2006.01)
A61B 5/11 (2006.01)
(Continued)

(52) U.S. Cl.
CPC .......... A63B 71/0622 (2013.01); A61B 5/112 (2013.01); A61B 5/486 (2013.01);
(Continued)

(58) Field of Classification Search
CPC . A63B 71/0622; A63B 71/0686; A63B 5/112; A63B 5/486; A63B 5/742;
(Continued)

(56) References Cited

U.S. PATENT DOCUMENTS 5,349,277 A * 9/1994 Takahashi ............ B62D 57/032
318/568.1
2011/0166488 A1 * 7/2011 Miyake .................... A61H 3/00
601/34
(Continued)

FOREIGN PATENT DOCUMENTS

CN 101583403 A 11/2009
CN 103657029 A 3/2014
(Continued)

OTHER PUBLICATIONS

Office Action issued over the corresponding Chinese Patent Application No. 201880019103.9 dated of Feb. 23, 2021, and the English translation thereof.
(Continued)

Primary Examiner — Jay Trent Liddle
Assistant Examiner — Alyssa N Brandley
(74) Attorney, Agent, or Firm — Carrier Blackman & Associates, P.C.; Joseph P. Carrier; William D. Blackman

(57) ABSTRACT

A walking support system is a walking support system which supports walking of a user, and includes a display unit, a landing timing detection unit configured to detect landing at the time of walking of the user, a target landing timing setting unit configured to set a target landing timing of the user on the basis of an output of the landing timing detection unit, and a display control unit configured to cause the display unit to display an auxiliary image prompting the user to land at the target landing timing.

8 Claims, 7 Drawing Sheets

(51) Int. Cl.
*A61B 5/00* (2006.01)
*G09B 19/00* (2006.01)
*G06F 3/01* (2006.01)

(52) U.S. Cl.
CPC .......... *A61B 5/742* (2013.01); *A63B 71/0686* (2013.01); *G09B 19/003* (2013.01); *A63B 2071/0666* (2013.01); *A63B 2071/0694* (2013.01); *A63B 2220/18* (2013.01); *A63B 2220/34* (2013.01); *A63B 2220/40* (2013.01); *A63B 2220/836* (2013.01); *G06F 3/011* (2013.01)

(58) Field of Classification Search
CPC .... A63B 2071/0694; A63B 2071/0666; A63B 2220/18; A63B 2220/34; A63B 2220/40; A63B 2220/836; G09B 19/003; G06F 3/011
See application file for complete search history.

(56) References Cited

U.S. PATENT DOCUMENTS

| | | | |
|---|---|---|---|
| 2014/0073481 A1* | 3/2014 | Al .................. | A63B 24/0084 482/1 |
| 2017/0027802 A1* | 2/2017 | Jang .................. | A61B 5/112 |
| 2018/0209814 A1* | 7/2018 | Yamada .................. | A61B 5/112 |

FOREIGN PATENT DOCUMENTS

| | | |
|---|---|---|
| CN | 106491311 A | 3/2017 |
| GB | 2 424 084 A | 9/2006 |
| JP | H05-254465 A | 10/1993 |
| JP | 2001-299980 A | 10/2001 |
| JP | 2003-164544 A | 6/2003 |
| JP | 2006-204730 A | 8/2006 |
| JP | 2010-264320 A | 11/2010 |
| JP | 2011-177278 A | 9/2011 |
| JP | 2016-073630 A | 5/2016 |

OTHER PUBLICATIONS

PCT/ISA/210 from International Application PCT/JP2018/011375 with the English translation thereof.

* cited by examiner

FIG. 1
(a) 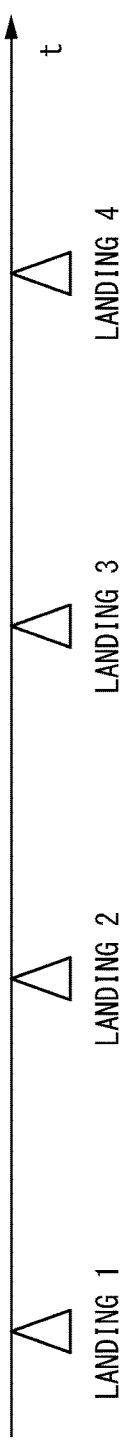
(b) 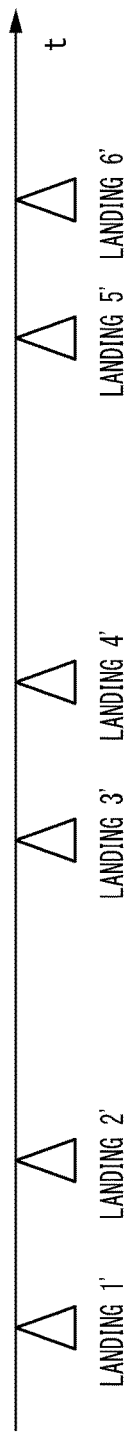

FIG. 7
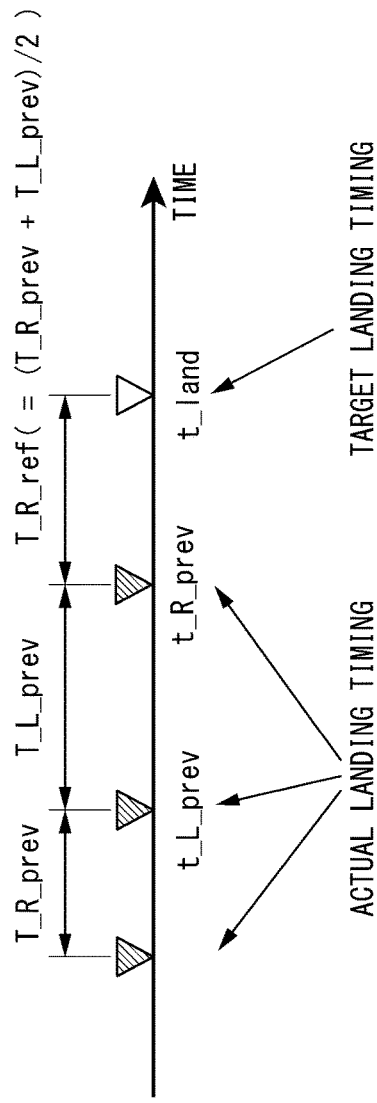
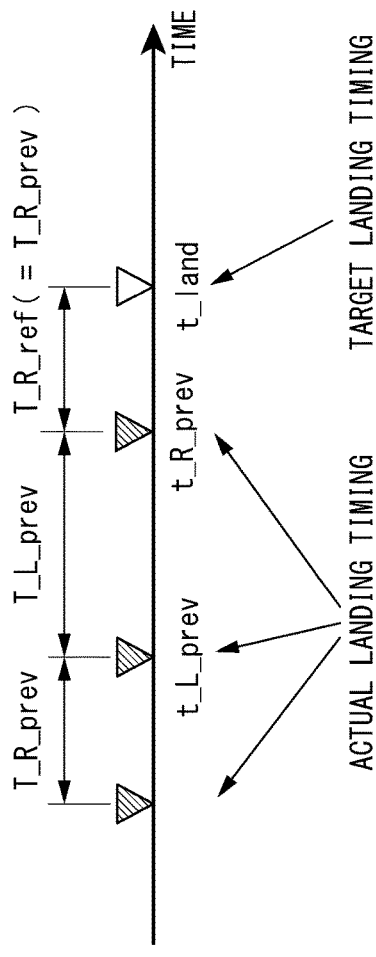

WALKING SUPPORT SYSTEM, WALKING SUPPORT METHOD, AND PROGRAM

TECHNICAL FIELD

The present invention relates to a walking support system, a walking support method, and a program.

Priority is claimed on Japanese Patent Application No. 2017-055720, filed Mar. 22, 2017, the content of which is incorporated herein by reference.

BACKGROUND ART

Conventionally, acquiring an exercise state of a person from sensors or the like attached to the human body and prompting a change in tempo of exercise using speech has been performed. For example, Patent Document 1 discloses an exercise support device which changes the tempo of music output based on a tempo of the current exercise of a user according to a difference between a target pulse rate and a current pulse rate.

CITATION LIST

Patent Literature

[Patent Document 1]
Japanese Unexamined Patent Application, First Publication No. 2001-299980

SUMMARY OF INVENTION

Technical Problem

However, in the technology described in Patent Document 1, an exercise support for physically disabled people (for example, a user with paralysis of one foot and having poor walking balance) is not considered. In addition, since change of the tempo of a motion is prompted using speech in the technology described in Patent Document 1, a user needs to change an exercise motion simultaneously with the speech which is heard, and it may be difficult to predict the next motion in advance.

The aspects of the present invention are made in view of the points described above, and an object thereof is to provide a walking support system, a walking support method, and a program which adjust a left/right balance at the time of walking of a user, and lead to a smooth walking motion.

Solution to Problem

In order to solve the above technical problems and achieve related objectives, the present invention has adopted the following aspects.

(1) According to one aspect of the present invention, a walking support system is a walking support system which supports walking of a user and includes a display, a landing timing detection unit configured to detect landing at the time of walking of the user, a target landing timing setting unit configured to set a target landing timing for the user on the basis of an output of the landing timing detection unit, and a display control unit configured to cause the display unit to display an auxiliary image prompting the user to land at the target landing timing.

(2) In the aspect of (1) described above, the target landing timing setting unit may set the target landing timing such that a time interval from landing of the left foot to landing of the right foot of the user and a time interval from the landing of the right foot to the landing of the left foot of the user become close to each other.

(3) In the aspect of (1) or (2) described above, the auxiliary image may be an image in which a remaining time before the target landing timing is recognizable.

(4) In the aspect of (3) described above, the display control unit may cause the display unit to display the auxiliary image in which a change of an object starts with landing of a first foot and the change of the object is completed at the target landing timing of a second foot.

(5) In the aspect of any one of (1) to (4) described above, the walking support system may further include an upper body angle detector configured to detect an angle of the upper body at the time of the walking of the user, and the target landing timing setting unit may set the target landing timing on the basis of an output of the upper body angle detector.

(6) In the aspect of (5) described above, the target landing timing setting unit may set the target landing timing to be advanced when the angle of the upper body is smaller than a predetermined value.

(7) In the aspect of (5) or (6) described above, the target landing timing setting unit may set the target landing timing to be delayed when the angle of the upper body is larger than the predetermined value.

(8) According to another aspect of the present invention, a walking support method includes, by a control computer of a walking support system, detecting landing at the time of walking of a user, setting a target landing timing of the user based on a result of the detection, and causing a display unit to display an auxiliary image prompting the user to land at the target landing timing.

(9) According to still another aspect of the present invention, a program is configured to cause a control computer of a walking support system to execute processing of detecting landing at the time of walking of a user, processing of setting a target landing timing of the user based on a result of the detection, and processing of causing a display unit to display an auxiliary image prompting the user to land at the target landing timing.

Advantageous Effects of Invention

According to aspects of the present invention, it is possible to adjust a left/right balance at the time of walking of a user, and lead to a smooth walking motion.

BRIEF DESCRIPTION OF DRAWINGS

FIG. 1 is a diagram which shows an outline of a walking support system.

FIG. 7 is a diagram which shows an example of setting of a target landing timing according to the second embodiment.

DESCRIPTION OF EMBODIMENTS

First, an outline of the present embodiment will be described. FIG. 1 is a diagram which shows an outline of a walking support system. FIG. 1(a) represents a landing timing of a healthy person at the time of walking, and FIG. 2(b) represents a landing timing of a pedestrian with paralysis of one foot. In FIG. 1, the horizontal axis represents time, and points indicated by triangles show landing timings of pedestrians.

At the time of walking, a healthy person usually lands at substantially constant timings such as landing 1, landing 2, landing 3, and landing 4 as shown in FIG. 1(a). In other words, a pace is almost constant. On the other hand, when a pedestrian with paralysis of one foot, as shown in FIG. 1(b), lands on a foot with paralysis (landing 1'), since a force when stepping with the shaft of the foot may be weak, the next step cannot be made large, and the next pace may become shortened. In other words, a next step after landing on a foot with paralysis is landing at a timing earlier than the previous step (landing 2'). Since the next step is made with a foot without paralysis serving as the shaft foot, the pace is relatively long. That is, a next step after landing on a foot without paralysis is landing at a timing later than the previous step (landing 3'). In this manner, the pedestrian with paralysis of one foot has different left and right landing timings, and thus tends to have poor walking balance.

The walking support system according to the present embodiment includes a landing timing detection unit which detects landing at the time of walking of a user, and a target landing timing setting unit which sets a target landing timing of a user on the basis of an output of the landing timing detection unit to solve the problems described above. Then, a display control unit causes a display unit to display an auxiliary image prompting a user to land at a target landing timing. The target landing timing is a timing of landing set as a target of a next step of a user, and is, for example, a timing of landing such that a time interval from landing of the left foot to landing of the right foot of the user and a time interval from the landing of the right foot to the lending landing of the left foot become close to each other. In the example of FIG. 1(b), for example, the timing of landing is made such that the timing of landing 2' is delayed and the timing of landing 3' is advanced. As a result, the user can land at the target landing timing by performing a landing operation according to the auxiliary image. That is, a walking support system can adjust the left/right balance at the time of walking of a user, and lead to a smooth walking motion.

First Embodiment

Figure 2:
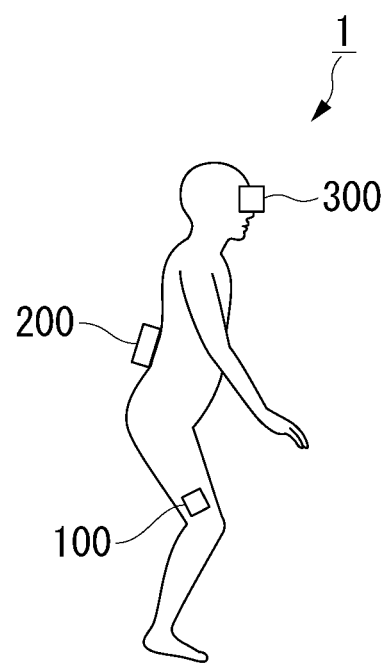
FIG. 2 is a diagram which shows an outline of the walking support system according to a first embodiment.

Next, a configuration of a first embodiment will be described. FIG. 2 is a diagram which shows an outline of a walking support system 1 according to the first embodiment of the present invention. The walking support system 1 includes a landing detection device 100, an upper body angle detection device 200, and a display device 300.

The landing detection device 100 includes, for example, an acceleration sensor. The landing detection device 100 is attached to the leg or the like of a user and acquires information for detecting a landing timing of a user. The landing detection device 100 may be attached to the foot or shoes of a user.

The upper body angle detection device 200 includes, for example, an inclination sensor including an angular speed sensor and an acceleration sensor. The upper body angle detection device 200 is attached to the waist, back, or the like of a user and is parallel with a width direction of the user's body, and acquires information for detecting the angle of the upper body of a user.

The display device 300 is an augmented reality (AR) device which displays additional information in real space in which a user visually recognizes it. In addition, the display device 300 may also be a virtual reality (VR) device which displays virtual reality. The display device 300 may be, for example, a glasses-type display or a head-mounted display which is attached to the head of a user. The display device 300 sets the target landing timing of a user on the basis of the information acquired from the landing detection device 100 or the upper body angle detection device 200, and displays an auxiliary image which prompts the user to land at the target landing timing. The details of the target landing timing and the auxiliary image will be described below.

The landing detection device 100 and the upper body angle detection device 200 are communicatively connected to the display device 300 in a wired or wireless manner. Note that the landing detection device 100, the upper body angle detection device 200, and the display device 300 may be configured as the same device. In addition, the landing detection device 100, the upper body angle detection device 200, and the display device 300 may also be configured as a part of a functional device such as a smartphone.

Figure 3:
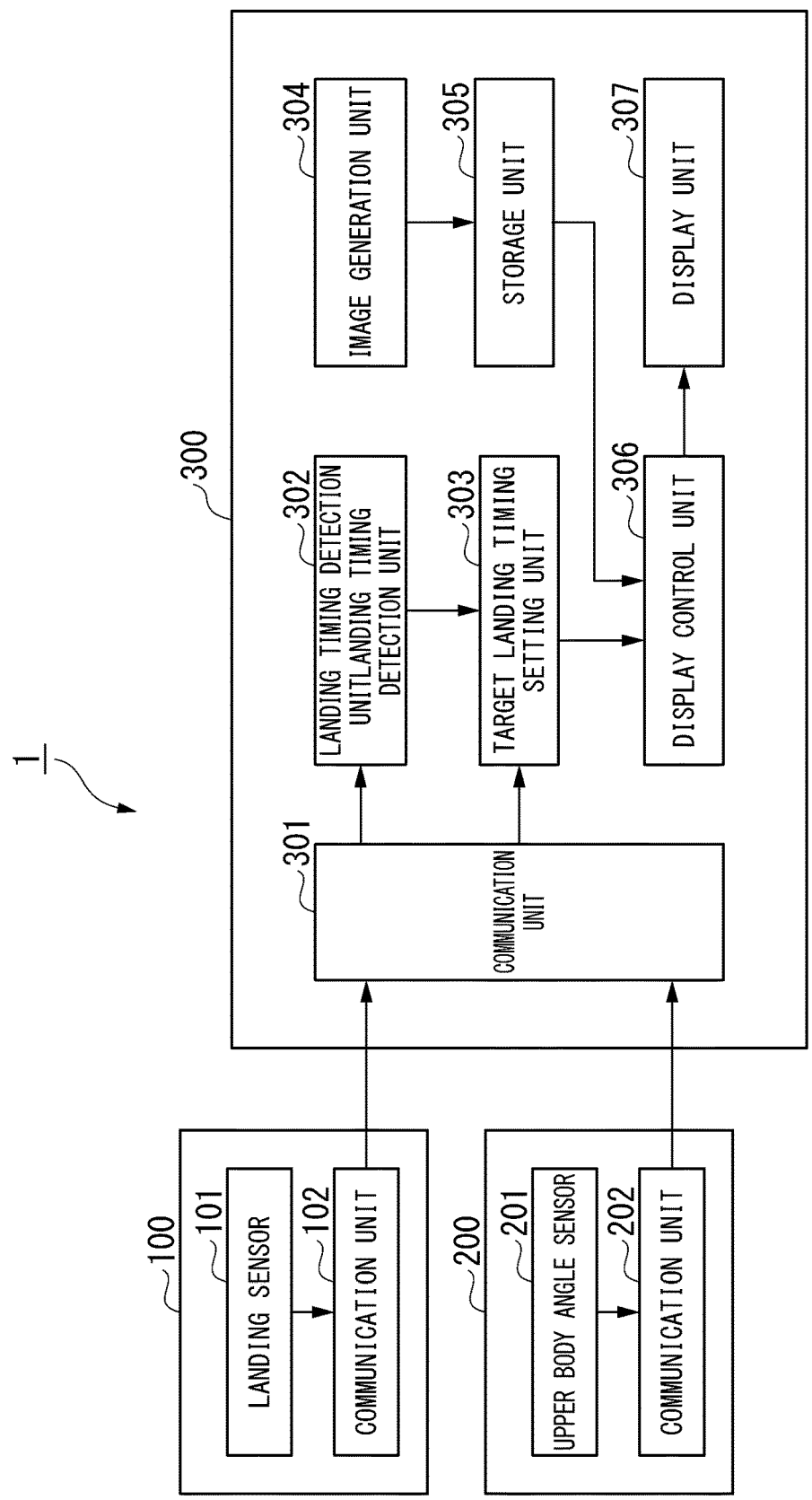
FIG. 3 is a block diagram which shows a configuration example of the walking support system according to the first embodiment.

FIG. 3 is a block diagram which shows a configuration example of the walking support system 1 according to the present embodiment. The walking support system 1 includes a landing detection device 100, an upper body angle detection device 200, and a display device 300.

The landing detection device 100 includes a landing sensor 101 and a communication unit 102. The landing sensor 101 acquires information for detecting a landing timing of a user. The landing sensor 101 is, for example, an acceleration sensor, and detects an acceleration which acts thereon. Since the landing detection device 100 is attached to the leg of a user, an acquired acceleration represents an acceleration of the leg of a user. The landing sensor 101 outputs the acquired acceleration to the communication unit 102. Note that the landing sensor 101 may be a sensor such as an angular speed sensor, a geomagnetic sensor, a vibration sensor, or the like, acquire information other than acceleration, and output it to the communication unit 102.

The communication unit 102 includes a communication interface for performing communication between devices via a wired or wireless network, and communicates with a communication unit 301 of the display device 300. The communication unit 102 outputs the acceleration of the leg of a user input from the landing sensor 101 to the communication unit 301.

The upper body angle detection device 200 includes an upper body angle sensor 201 and a communication unit 202. The upper body angle sensor 201 detects an angle of the upper body of a user with respect to the ground. The upper body angle sensor 201 is, for example, a combination of an angular speed sensor, an acceleration sensor, and an integration operator, calculates the angle of the upper body of a user by processing an integration operation of detected angular speeds, and further corrects the calculated angle of the upper body using an acceleration sensor. In addition, the upper body angle sensor 201 may also detect an angle of the upper body with respect to the lower body of a user on the basis of acquisition information of an angle sensor attached to a hip joint or the like or the user. The upper body angle sensor 201 outputs the acquired angle of the upper body of a user to the communication unit 202.

The communication unit 202 includes a communication interface for performing communication between devices via the wired or wireless network, and communicates with the communication unit 301 of the display device 300. The communication unit 202 outputs the angle of the upper body of a user input from the upper body angle sensor 201 to the communication unit 301.

The display device 300 includes the communication unit 301, a landing timing detection unit 302, a target landing timing setting unit 303, an image generation unit 304, a storage unit 305, a display control unit 306, and a display unit 307. The landing timing detection unit 302, the target landing timing setting unit 303, the image generation unit 304, and the display control unit 306 are realized by, for example, a processor such as a central processing unit (CPU) or the like executing programs. In addition, a part or all of these may be realized by hardware such as a large scale integration (LSI), an application specific integrated circuit (ASIC), or a field-programmable gate array (FPGA), and may also be realized by cooperation between software and hardware.

The communication unit 301 includes a communication interface for performing communication between devices via a wired or wireless network, and communicates with the communication unit 102 of the landing detection device 100 and communication unit 202 of the upper body angle detection device 200. The communication unit 301 outputs the acceleration of the leg of a user input from the communication unit 102 to the landing timing detection unit 302. In addition, the communication unit 301 outputs the angle of the upper body of a user input from the communication unit 202 to the target landing timing setting unit 303.

The landing timing detection unit 302 acquires an acceleration of the leg of a user input from the landing detection device 100 via the communication unit 301. The landing timing detection unit 302 detects a landing timing of the user on the basis of the acquired acceleration. The landing timing detection unit 302 calculates, for example, a speed of the leg of a user by performing integration operation processing on the acquired acceleration, and detects a timing at which a downward speed changes from positive to negative as a timing at which the user lands. Alternatively, the landing timing detection unit 302 may detect a timing at which the acceleration changes rapidly to above a predetermined value as the timing at which the user lands. The landing timing detection unit 302 outputs the detected landing timing of the user to the target landing timing setting unit 303. Note that the processing of the landing timing detection unit 302 may be performed by the landing detection device 100, and the landing timing of the user detected by the landing detection device 100 may be acquired and output to the target landing timing setting unit 303. In addition, the landing timing detection unit 302 may detect a landing timing using a means for estimating a walking phase, for example, a technology described in U.S. Pat. No. 5,938,124.

The target landing timing setting unit 303 sets a target landing timing of a user on the basis of the landing timing of the user input from the landing timing detection unit 302. The target landing timing is a landing timing serving as a target of a next step of the user. The target landing timing setting unit 303 sets a timing such that the time interval from landing of the left foot to landing of the right foot of the user and the time interval from the landing of the right foot to the landing of the left foot become close to each other. More specifically, for example, the target landing timing setting unit 303 may obtain an average value of an interval between a current landing timing and a previous landing timing and an interval between the previous landing timing and the next previous landing timing, and set a target landing timing such that the average value is an interval between the current landing timing and the next landing timing.

The target landing timing setting unit 303 does not necessarily have to determine the landing of the right foot and the landing of the left foot of a user, and may set a next target landing timing on the basis of a history of landing timings of the user in the past. When it is determined whether a landing is with the right foot or the left foot of a user, the target landing timing setting unit 303 acquires, for example, whether a paralyzed foot of a user is the right foot or the left foot from user information, and determines whether a landing foot is the right foot or the left foot on an assumption that the shaft foot at the time of a landing timing being advanced is a foot with paralysis. Similarly, the target landing timing setting unit 303 may acquire various types of user information (degree of disability, degree of muscle strength), and use these as parameters at the time of setting a target landing timing. The user information may be registered in the storage unit 305 in advance, and may also be acquired from outside. In addition, the target landing timing setting unit 303 may set an upper body angle of a user input from the upper body angle detection device 200 as a parameter at the time of setting a target landing timing. The target landing timing setting unit 303 outputs a set target landing timing to the display control unit 306.

The image generation unit 304 generates an auxiliary image (and an image to be its material) prompting a user to land at a target landing timing. The auxiliary image is additionally displayed on a real space on which the user visually recognizes it. In addition, the auxiliary image may be additionally displayed in a virtual space displayed by the display device 300. Moreover, the auxiliary image may be a still image of one frame or may be a moving image (video) including a plurality of frames. A specific example of the auxiliary image will be described below. The image generation unit 304 outputs the generated auxiliary image to the storage unit 305.

The storage unit 305 includes, for example, a hard disc drive (HDD), a flash memory, an electrically erasable programmable read only memory (EEPROM), a read only memory (ROM), a random access memory (RAM), and the like, and stores various programs such as firmware or application programs to be executed by a processor such as a CPU included in the display device 300 or results and the like of processing executed by a processor. The storage unit 305 holds an auxiliary image input from the image generation unit 304, and outputs the auxiliary image to the display control unit 306 in accordance with a request of the display control unit 306. Note that the storage unit 305 may output an auxiliary image registered from the outside in advance to the display control unit 306.

The display control unit 306 controls a function relating to an image display of the display device 300. The display control unit 306 causes the display unit 307 to display an auxiliary image which prompts a user to land at a target landing timing on the basis of the target landing timing input from the target landing timing setting unit 303. The details of the operation of the display control unit 306 will be described below.

The display unit 307 is, for example, a glasses-type display or a head-mounted display, and displays various types of images including an auxiliary image on a display on the basis of a control of the display control unit 306. The display unit 307 may display an auxiliary image on a transmission-type display in a two-dimensional manner, and may also display an auxiliary image in a three-dimensional manner using a 3D display such as in a polarization glasses method or a liquid crystal shutter glasses method. In addition, the display unit 307 may display an auxiliary image on an external screen by projection without using a display, or may display a stereoscopic image using an optical technology such as holography. In this case, the display device 300 does not have to be attached to a user.

Figure 4:
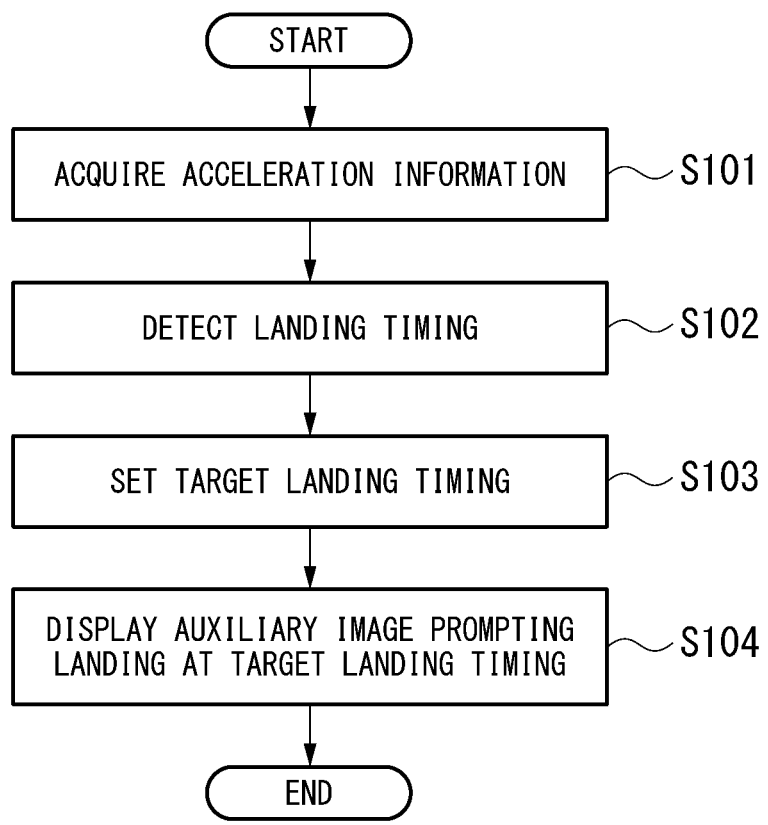
FIG. 4 is a flowchart which shows a processing example of the walking support system according to the first embodiment.

Next, an operation of the walking support system 1 according to the present embodiment will be described. FIG. 4 is a first flowchart which shows a processing example of the walking support system 1 according to the present embodiment.

First, the landing timing detection unit 302 of the display device 300 acquires the acceleration of the leg of a user input from the landing detection device 100 via the communication unit 301 (step S101).

Next, the landing timing detection unit 302 detects the landing timing of a user on the basis of the acquired acceleration (step S102). The landing timing detection unit 302 calculates, for example, a speed of the leg of a user, and detects a timing at which a downward speed changes from positive to negative as a landing timing of a user. Alternatively, the landing timing detection unit 302 detects a timing at which the acceleration changes rapidly above a predetermined value as the landing timing of a user. Thereafter, the landing timing detection unit 302 outputs the detected landing timing of a user to the target landing timing setting unit 303. In addition, the landing timing detection unit 302 may detect a landing timing using the means for estimating a walking phase, for example, the technology described in U.S. Pat. No. 5,938,124.

Next, the target landing timing setting unit 303 sets a target landing timing on the basis of the input landing timing of a user (step S103). The target landing timing setting unit 303 sets a next target landing timing such that the time interval from landing of the left foot to landing of the right foot of a user and the time interval from the landing of the right foot to the landing of the left foot become close to each other. The target landing timing setting unit 303 outputs the set target landing timing to the display control unit 306.

Next, the display control unit 306 acquires an auxiliary image prompting a user to land at the input target landing timing from the storage unit 305, and causes the display unit 307 to display it (step S104). An example of the auxiliary image will be described below. Note that the display unit 307 may acquire an auxiliary image from the storage unit 305 in advance, and hold it.

Figure 5:
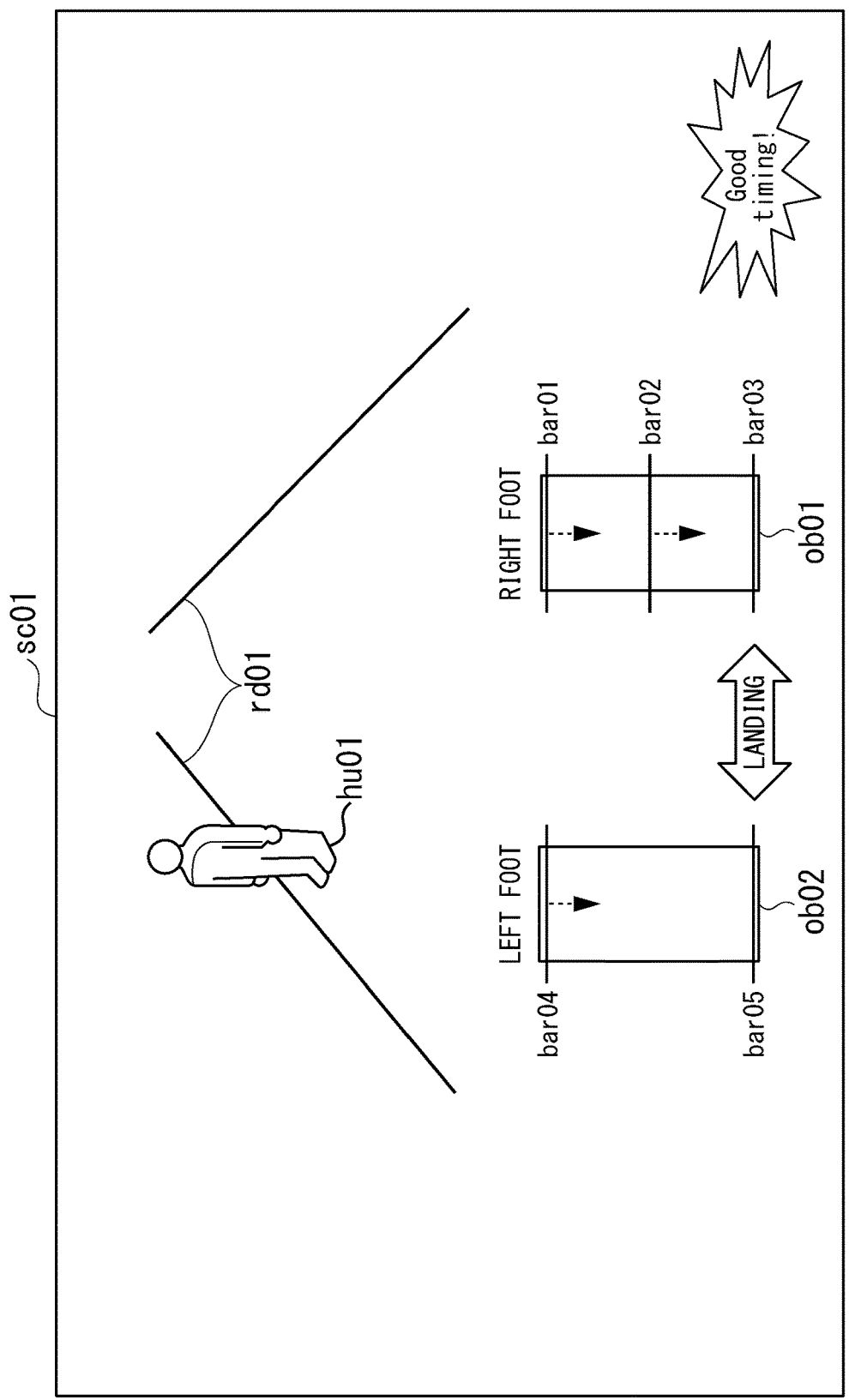
FIG. 5 is a diagram which shows an example of an auxiliary image according to the first embodiment.

Subsequently, an auxiliary image according to the present embodiment will be described. FIG. 5 is a diagram which shows an example of the auxiliary image according to the present embodiment. sc01 in FIG. 5 represents a forward field of vision seen by a user via the display unit 307. In this example, a human 01 and a road rd01 are present in sc01. A human hu01 and a road rd01 may be an actual human and road visually recognized via the display unit 307, and may be virtually displayed by the display device 300.

The display control unit 306 overlaps the human h01 and the road rd01 at a bottom of sc01, and causes images ob01 and ob02 to be displayed. An image ob01 displayed on a right side from a user is an image indicating a target landing timing of the right foot of the user, and an image ob02 displayed on a left side from the user is an image indicating a target landing timing of the left foot of the user. An upper end of the image ob01 indicates a timing at which the left foot of the user lands, and a lower end of the image ob01 indicates a target timing at which the right foot of the user needs to land next time. The display control unit 306 displays a bar (bar01) at the upper end of the image ob01 at the same time as the user lands the left foot, and causes the bar to slide downward at a constant speed. Then, the display control unit 306 causes the bar (bar03) to reach the lower end of the image ob01 at a target timing at which the right foot of the user needs to land next time.

The user sees a falling bar at a constant speed and determines a next timing to land. Specifically, the right foot of the user tries to land at the same time as a timing at which the falling bar reaches the lower end of ob01 (bar03). If the user lands the right foot, the display control unit 306 displays the bar at the upper end of the image ob02 (bar04), and causes the bar to fall at a constant speed. Then, the display control unit 306 causes the bar to reach the lower end of the image ob02 at a target landing timing of the left foot (bar05). The display control unit 306 displays the bar at the upper end of the image ob01 again (bar01) and repeats this processing afterward if the user lands the left foot.

As a result, the user can recognize remaining time according to the bar falling at the same speed and can easily predict a next landing timing in advance. For example, even when the user usually lands the right foot at a timing of bar2, the user endures and delays landing until a timing of bar3 that is a target landing timing. That is, the user can walk each one step at a time close to ideal landing timings, and can walk with good left/right balance.

Note that, when the user lands within a certain error range from the target landing timing, voice and video may be used to notify of a good timing or to add points on a game.

As a result, the user can perform walking with fun according to a target landing timing in a game-like manner. In addition, it is not necessary to display auxiliary images for the right foot and the left foot, respectively, and only a next landing time may be indicated using one image. Moreover, a display image is not limited to the example in FIG. 5, and may be displayed in another form. A display position of the display image is not also limited to the bottom of sc01, and may be disposed on a side of sc1 or may be translucently displayed in front of the field of vision. In addition, the display of a bar may be performed using another object (such as the form of a foot).

As described above, the walking support system 1 according to the present embodiment includes the display unit 307, the landing timing detection unit 302 configured to detect landing at the time of walking of a user, the target landing timing setting unit 303 configured to set a target landing timing of a user on the basis of an output of the landing timing detection unit 302, and the display control unit 306 configured to cause the display unit 307 to display an auxiliary image prompting a user to land at the target landing timing. As a result, it is possible to adjust the left/right balance at the time of walking of a user, and to lead to a smooth walking motion.

In addition, in the walking support system 1 according to the present embodiment, the target landing timing setting unit 303 may set a target landing timing such that the time interval from landing of the left foot to landing of the right foot of a user and the time interval from the landing of the right foot to the landing of the left foot of the user are close to each other. As a result, left and right paces at the time of walking are close to each other, and a user can perform walking with a good left/right balance.

In addition, in the walking support system 1 according to the present embodiment, an auxiliary image may be an image in which remaining time before the target landing timing is recognizable. As a result, a user can easily predict the next landing timing.

In addition, in the walking support system 1 according to the present embodiment, the display control unit 306 may cause the display unit 307 to display an auxiliary image in which a change of an object starts with the landing of a first foot and the change of the object is completed at a target landing timing of a second foot. As a result, a user can more easily adjust a landing timing according to the change of the object.

Second Embodiment

Hereinafter, a second embodiment of the present invention will be described with reference to the drawings. Note that constituents the same as in the embodiment described above will be denoted by the same reference numerals, and the descriptions thereof will be omitted here. A configuration of a walking support system 2 according to the present embodiment is the same as that of the walking support system 1 according to the first embodiment. In the walking support system 2, setting of a target landing timing is performed using an angle of the upper body of a user in addition to the processing in the first embodiment.

Figure 6:
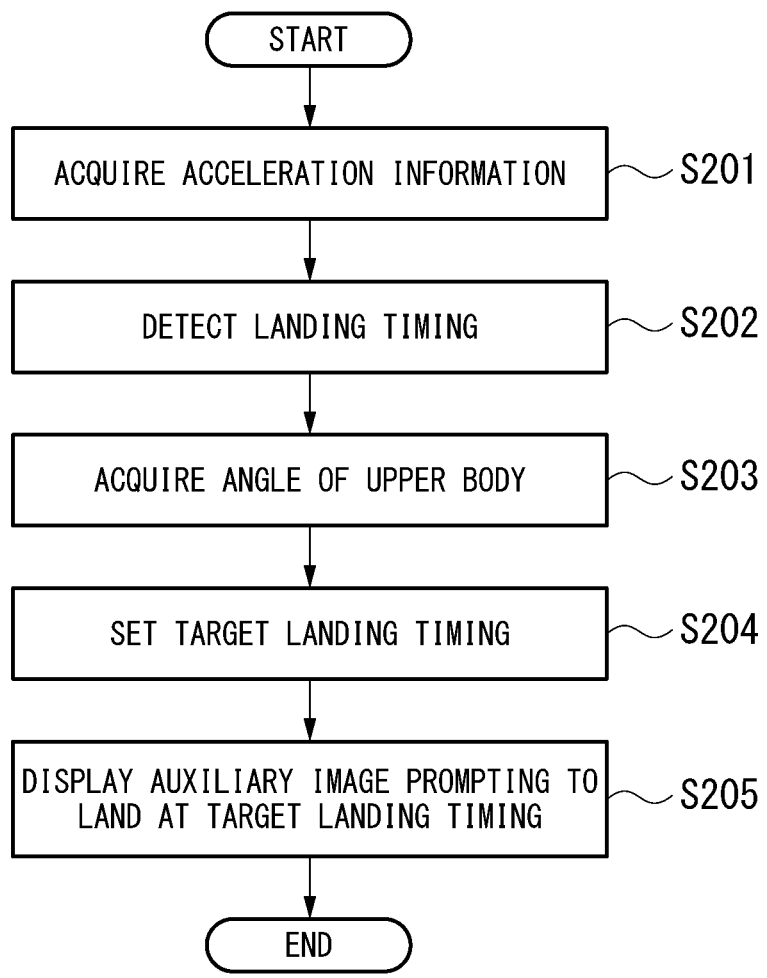
FIG. 6 is a flowchart which shows a processing example of a walking support system according to a second embodiment.

FIG. 6 is a flowchart which shows a processing example of the walking support system 2 according to the present embodiment.

First, the landing timing detection unit 302 of the display device 300 acquires an acceleration of the leg of a user input from the landing detection device 100 via the communication unit 301 (step S201).

Next, the landing timing detection unit 302 detects a landing timing of a user on the basis of the acquired acceleration (step S202). Thereafter, the landing timing detection unit 302 outputs the detected landing timing of a user to the target landing timing setting unit 303.

Next, the target landing timing setting unit 303 acquires the angle of the upper body of a user input from the upper body angle detection device 200 via the communication unit 301 (step S203). Note that the processing of step S203 may also be executed before the processing of step S201 and step S203.

Next, the target landing timing setting unit 303 sets a target landing timing on the basis of the acquired landing timing of a user and the acquired angle of the upper body of a user (step S204). The target landing timing setting unit 303 sets a target landing timing calculated on the basis of a landing timing to be advanced, for example, when the angle of the upper body of a user with respect to the ground is smaller than a predetermined value, that is, when the user leans forward by a certain degree or more. This is because it is difficult for the user to make the next step taken large when the user is leaning forward by a certain degree or more, and it is possible to suppress the user from unreasonably making a large step. In addition, the target landing timing setting unit 303 may set the target landing timing calculated on the basis of a landing timing to be delayed when the angle of the upper body of a user with respect to the ground is larger than a predetermined value, that is, when the angle of the upper body of a user is close to being perpendicular to the ground. This is because it is easy to make a next step taken large when the upper body of a user is close to being perpendicular to the ground. More general setting examples of a target landing timing will be described below.

Next, the display control unit 306 acquires an auxiliary image for prompting a user to land at an input target landing timing from the storage unit 305, and causes the display unit 307 to display it (step S205). An example of the auxiliary image is the same as that of the first embodiment.

Next, an example of the setting of a target landing timing will be described with reference to FIG. 7. FIG. 7 is a diagram which shows the example of the setting of a target landing timing according to the present embodiment.

When the right foot of a user is currently grounded, a target time T_R_ref from the landing of the right foot to landing of the left foot may be expressed by Equation (1).

[Math. 1]

$$T\_R\_ref=(T\_R\_prev+T\_L\_prev)/2+k1*(T\_R\_prev-T\_L\_prev)/2+k2*(\theta+k3*\theta dot-C) \quad (1)$$

A target landing timing t_land at this time may be represented according to Equation (2).

[Math. 2]

$$t\_land=t\_L\_prev+T\_R\_ref \quad (2)$$

In addition, when the left foot of a user is currently grounded, a target time T_L_ref from the landing of the left foot to landing of the right foot may be expressed by Equation (3).

[Math. 3]

$$T\_L\_ref=(T\_R\_prev+T\_L\_prev)/2-k1*(T\_R\_prev-T\_L\_prev)/2+k2*(\theta+k3*\theta dot-C) \quad (3)$$

The target landing timing t-land at this time may be represented according to Equation (4).

[Math. 4]

$$t\_land=t\_R\_prev+T\_L\_ref \quad (4)$$

Here, t_R_prev represents a time at which the right foot actually landed the previous time, t_L_prev represents a time at which the left foot actually landed the previous time. T_R_prev represents an average value of time taken from the actual landing of the right foot at a previous time to the landing of the left foot, or time taken from the landing of the right foot to the landing of the left foot several steps before. T_L_prev is an average value of time taken from the actual landing of the left foot at a previous time to the landing of the right foot, or time taken from the landing of the left foot to the landing of the right foot several steps before. $\theta$ represents an upper body angle at a predetermined timing. However, a state in which the upper body stands vertically is set as $\pi/2$[rad] (90 degrees), and a state in which the upper body is bent by $\pi/2$[rad] (90 degrees) before this state is set as 0 [rad] (0 degrees). $\theta$dot represents an upper body angular speed at a predetermined timing. k1 represents a predetermined constant ($0 \leq k1 \leq 1$). k2 represents a predetermined constant. k3 represents a predetermined constant ($0 \leq k3$). C represents a predetermined positive constant.

When setting is performed as described above, it is possible to adjust characteristics of induction by a combination of set values of the constants k1, k2, k3, and C. For example, if k1=0, k2=0, k3=0, and C=0, as shown in FIG. 7(a), a target landing timing does not depend on an angle of the upper body, and there is no difference between a left and a right target landing timing. In addition, if k1=1, k2=0, k3=0, and C=0, as shown in FIG. 7(b), the target landing timing does not depend on the angle of the upper body, and the difference between left and right target landing timings is equal to a difference between actual left and right landing timings of a user.

If k1=0, k2=0, k3≠0, and C=0, the difference between left and right target landing timings does not depend on the difference between actual left and right landing timings of a user, and depends on the angle of the upper body. In addition, if k1=0, k2=0, k3≠0, and C≠0, the difference between left and right target landing timings does not depend on the difference between actual left and right landing timings of a user, and depends on the angle of the upper body and an angular speed of the upper body. Note that in the above equation, a term of (θ+k3*θdot−C) may be set to zero in the case of being positive.

As described above, the walking support system 2 according to the present embodiment includes the display unit 307, the landing timing detection unit 302 configured to detect landing at the time of walking of a user, the target landing timing setting unit 303 configured to set a target landing timing of a user on the basis of an output of the landing timing detection unit 302, and the display control unit 306 configured to cause the display unit 307 to display an auxiliary image prompting a user to land at the target landing timing. Furthermore, a upper body angle detector (the upper body angle detection device 200) configured to detect an angle of the upper body at the time of walking of a user is further included, and the target landing timing setting unit 303 sets a target landing timing on the basis of an output of the upper body angle detector (the upper body angle detection device 200). As a result, it is possible to set a more appropriate target landing timing in consideration of an angle of the upper body of a user, and to lead to a smooth walking motion.

In addition, in the walking support system 2 according to the present embodiment, the target landing timing setting unit 303 may set a target landing timing to be advanced when the angle of the upper body is smaller than a predetermined value. As a result, it is possible to set a target landing timing in a more appropriate manner.

In the walking support system 2 according to the present embodiment, the target landing timing setting unit 303 may set a target landing timing to be delayed when the angle of the upper body is greater than the predetermined value. As a result, it is possible to set a target landing timing in a more appropriate manner.

As described above, the embodiments of the present invention have been described in detail with reference to the drawings, but a specific configuration is not limited to these embodiments, and includes a design change and the like within a range not departing from the gist of this invention. For example, the order of processing procedures, sequences, flowcharts, and the like in each embodiment may be changed as long as there are no contradictions with the features described in the claims.

In addition, various modifications can be made in one aspect of the present invention within the scope of the claims, and embodiments obtained by appropriately combining technical means respectively disclosed in different embodiments are included in the technical scope of the present invention. Moreover, a constituent that is an element described in respective embodiments and modifications described above and is substituted with an element having the same effect is also included.

For example, the embodiment described above may be used in combination with a walking assistance device. The walking assistance device is a walking training device which supports efficient walking based on an "inverted pendulum model." In the walking assistance device, motion of a hip joint at the time of walking is detected by an angle sensor embedded in left and right motors, and a control computer drives the motors. As a result, kicking-out of a lower leg caused by extension and induction of swinging of the lower leg due to a flexion of the hip joint is induced. By using the present embodiment in combination with the walking assistance device, it is possible to appropriately induce a landing timing that cannot be covered in the walking assistance device, and to perform a more effective walking support.

REFERENCE SIGNS LIST 1, 2 Walking support system
100 Landing detection device
101 Landing sensor
102 Communication unit
200 Upper body angle detection device
201 Upper body angle sensor
202 Communication unit
300 Display device
301 Communication unit
302 Landing timing detection unit
303 Target landing timing setting unit
304 Image generation unit
305 Storage unit
306 Display control unit
307 Display unit

The invention claimed is:

1. A walking support system which supports walking of a user, the walking support system comprising:
   a display;
   a landing timing detection circuitry configured to detect landing at the time of walking of the user;
   a target landing timing setting circuitry configured to set a target landing timing of the user on the basis of an output of the landing timing detection circuitry; and
   a display control circuitry configured to cause the display to display an auxiliary image prompting the user to land at the target landing timing,
   wherein the auxiliary image includes an image separately presenting a first object and a second object in which remaining time before the target landing timing is presented, and
   the display control circuitry causes the display to display the auxiliary image in which a change of the first object starts with landing of a first foot and the change of the first object is completed at the target landing of a second foot, and in which a change of the second object starts with landing of the second foot and the change of the second object is completed at the target landing of the first foot.

2. The walking support system according to claim 1, wherein the target landing timing setting circuitry is configured to set the target landing timing such that a time interval from landing of the left foot to landing of the right foot of the user and a time interval from the landing of the right foot to the landing of the left foot of the user become close to each other.

3. The walking support system according to claim 1, further comprising:
   an upper body angle detector configured to detect an angle of an upper body of the user at the time of the walking of the user,
   wherein the target landing timing setting circuitry is configured to set the target landing timing on the basis of an output of the upper body angle detector.

4. The walking support system according to claim 3, wherein the target landing timing setting circuitry is configured to set the target landing timing to be advanced when the angle of the upper body is smaller than a predetermined value.

5. The walking support system according to claim 3, wherein the target landing timing setting circuitry is configured to set the target landing timing to be delayed when the angle of the upper body is larger than a predetermined value.

6. A walking support method effected by a walking support system including a control computer, the walking support method comprising steps of:
   detecting, by the control computer, landing at the time of walking of a user;
   setting, by the control computer, a target landing timing of the user based on a result of the detecting step;
   causing, by the control computer, a display to display an auxiliary image prompting the user to land at the target landing timing,
   wherein the auxiliary image includes an image separately presenting a first object and a second object in which remaining time before the target landing timing is presented, and
   causing the display to display the auxiliary image in which a change of the first object starts with landing of a first foot and the change of the first object is completed at the target landing of a second foot, and in which a change of the second object starts with landing of the second foot and the change of the second object is completed at the target landing of the first foot.

7. A non-transitory computer-readable storage medium which is configured to cause a walking support system including a control computer to execute
   processing of detecting, by the control computer, landing at the time of walking of a user;
   processing of setting, by the control computer, a target landing timing of the user based on a result of the detection;
   processing of causing, by the control computer, a display to display an auxiliary image prompting the user to land at the target landing timing,
   wherein the auxiliary image includes an image separately presenting a first object and a second object in which remaining time before the target landing timing is presented, and
   processing of causing the display to display the auxiliary image in which a change of the first object starts with landing of a first foot and the change of the first object is completed at the target landing of a second foot, and in which a change of the second object starts with landing of the second foot and the change of the second object is completed at the target landing of the first foot.

8. The walking support system according to claim 1, wherein the display control circuitry is configured to cause the display to display a forward field of vision of where the user is walking together with the auxiliary image, and the auxiliary image includes a visual component which moves at a timing which prompts the user to land at the target landing timing.

* * * * *